Figure 1:
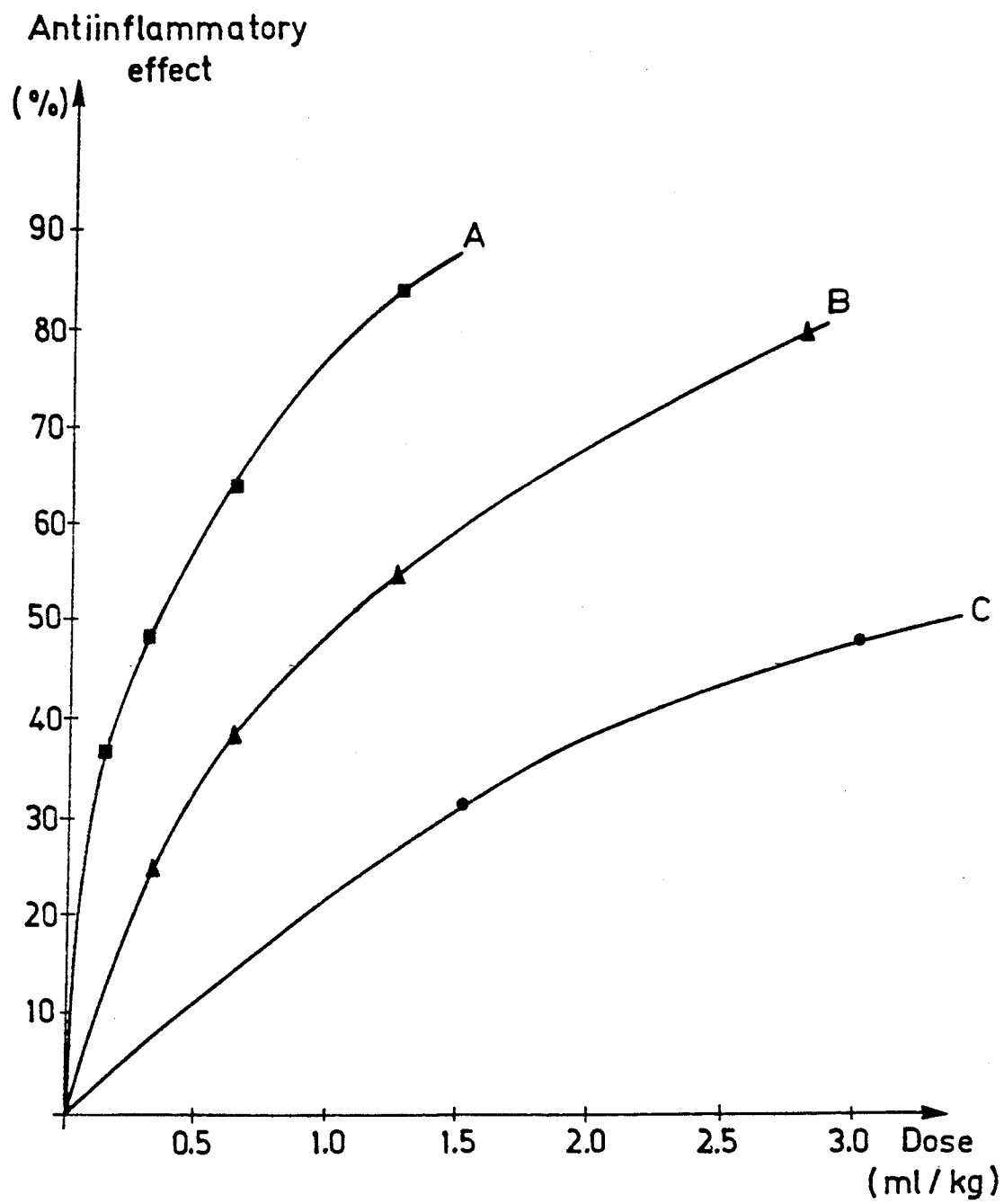

United States Patent [19]

Hangay et al.

[11] Patent Number: 5,080,901
[45] Date of Patent: Jan. 14, 1992

[54] COSMETIC AND PARAMEDICINAL COMPOSITIONS CONTAINING PLANT EXTRACTS

[75] Inventors: György Hangay; András Kelen; Katalin Ranky née Szita, all of Budapest; András Gulyás, Kerepestarcsa; Emilia Simonovits, Budapest; Judit Vincze née Kutrovics, Kerepestarcsa; Gábor Szepesi, Budapest; Péter Keserű, Budapest; András Selmeczi, Budapest; Pál Putz, Esztergom, all of Hungary

[73] Assignee: Richter Gedeon Vegyeszeti Gyar Rt., Budapest, Hungary

[21] Appl. No.: 370,776

[22] Filed: Jun. 23, 1989

[30] Foreign Application Priority Data

Jun. 24, 1988 [HU] Hungary ............... 3210/88

[51] Int. Cl.⁵ ............... A61K 35/78; A61K 47/00
[52] U.S. Cl. ............... 424/195.1; 514/783; 514/844
[58] Field of Search ............... 424/195.1

[56] References Cited

U.S. PATENT DOCUMENTS

| 58,106 | 9/1866 | Kieffer | 424/195.1 |
|---|---|---|---|
| 74,940 | 2/1868 | Rambaut | 424/195.1 |
| 82,696 | 10/1868 | Dennen | 424/195.1 |
| 86,331 | 1/1869 | Vann | 424/195.1 |
| 86,551 | 2/1869 | Jenkins | 424/195.1 |
| 93,209 | 8/1869 | Llado | 424/195.1 |
| 95,209 | 9/1869 | Draper | 424/195.1 |
| 102,686 | 5/1870 | Landert | 424/195.1 |
| 116,906 | 7/1871 | Williams | 424/195.1 |
| 208,064 | 9/1878 | Blosser | 424/195.1 |
| 229,804 | 7/1880 | Christopher | 424/195.1 |
| 308,900 | 12/1884 | Kieffer | 424/195.1 |
| 395,824 | 1/1889 | Gentry | 424/195.1 |

OTHER PUBLICATIONS

Gizella Verzar-Petri et al.: Medicinal Plants in the Therapy, pp. 55, 59, 92, 93.
Ed. Walter de Gruyter: Pocket-Book of the Knowledge of Drugs, pp. 10, 11, 48, 49.
Bela Issekutz: Prescription of Drugs, pp. 578, 583.
Hans Braun: Lexicon of Medicinal Plants for Physicians and Pharmacists, p. 155.
M. Pahlow: The Great Book of Medicinal Plants Health by means of the Healing Capacity of Nature, pp. 212, 213, 343, 344.
Steinmetz, Codex Vegetabilis 1957.

*Primary Examiner*—Johnnie R. Brown
*Assistant Examiner*—Ralph Gitomer
*Attorney, Agent, or Firm*—Keil & Weinkauf

[57] ABSTRACT

The invention relates to a novel cosmetic and paramedicinal active ingredient composition, particularly with an antiinflammatory and skin-calming effect, which comprises 0.005 to 5.0% by weight of an aqueous-ethanolic extract of Marigold,
0.005 to 2.0% by weight of an aqueous-ethanolic extract of Horse-chestnut
0.005 to 2.0% by weight of an aqueous-ethanolic extract of Licorice (sweet-root),
0.005 to 2.0% by weight of an aqueous Silver-weed extract,
0.005 to 2.0% by weight of an aqueous extract of Walnut-tree leaves,
0.002 to 1.0% by weight of Lavender resinoid and
0.001 to 0.2% by weight of Roman camomile oil as calculated for the total weight; as well as 85 to 99% by weight of a 35 to 60% by weight ethanol-water mixture as carrier.

The above preparation serves as a base material for excellent cosmetic compositions, curative cosmetics and curative products.

3 Claims, 3 Drawing Sheets

COSMETIC AND PARAMEDICINAL COMPOSITIONS CONTAINING PLANT EXTRACTS

The present invention relates to a cosmetic and paramedicinal composition with an increased effect, particularly with an antiinflammatory or skin anti-irritant effect.

It is known that, in the last decade, research in the cosmetics field shows a preference for the medicinal plants and their extracts. In many cases, an unexpected synergetic effect could be obtained by the combined use of preparations and extracts earlier used in the popular medicine or scientific therapy.

A good example of such a recognition is represented by the composition consisting of 5 or 10, respectively, various medicinal extracts which has formed the basis of the successful product family commercially available under the trade name "Richtofit" and which was described in the Hungarian patent specification No. 190,391.

Our research work has been aimed to develop a more effective composition starting from the above principle.

Thus, the aim of the present invention is to develop a combination of active ingredients consisting of plant extracts of native origin which may be capable of exceeding the prior art product(s) in one or more useful properties.

The invention is based on the recognition that a combination of active ingredients with a synergistic effect can be composed by omitting or replacing the components defined in the patent specification cited above as well as by varying the ratio of the original components.

Thus, the invention relates to an active ingredient composition, preferably with an antiinflammatory and skin anti-irritant effect, respectively, which comprises 0.005 to 5.0% by weight of an aqueous-ethanolic extract of Marigold,
0.005 to 2.0% by weight of an aqueous-ethanolic extract of Horse-chestnut,
0.005 to 2.0% by weight of an aqueous-ethanolic extract of Licorice (sweet-root),
0.005 to 2.0% by weight of an aqueous Silver-weed extract,
0.005 to 2.0% by weight of an aqueous extract of Walnut-tree leaves,
0.002 to 1.0% by weight of Lavender resinoid and
0.001 to 0.2% by weight of Roman camomile oil as calculated for the total weight; as well as
85 to 99% by weight of a 35 to 60% by weight ethanol-water mixture as carrier.

The invention further relates to cosmetic preparations, paramedicinal cosmetics and paramedicinal products containing 1 to 50% by weight of the above composition and optionally
0.01 to 0.5% by weight of menthol,
0.02 to 0.5% by weight of citric acid,
0.02 to 1.0% by weight of d-panthenol,
0.05 to 0.5% by weight of allantoin,
0.05 to 2.0% by weight of 2,4,4'-trichloro-2-hydroxydiphenyl ether,
0.5 to 5.0% by weight of a natural moisturizing factor and
0.5 to 50.0% by weight of ethanol as active ingredients and partly as a carrier in the case of ethanol; furthermore vehicles, additives and auxiliary materials, preferably water, glycerol, propylene glycol, polyethylene glycol, polyoxyethylene-sorbitan fatty acid esters, wax alcohols, coconut fatty acid diethanolamide, coconut fatty acid-propyl-betaine as well as solubilizing, stabilizing agents and flavor compositions in an amount of 50 to 98% by weight in the form of e.g. a cream, liquid emulsion, lotion, bath and shampoo compositions with a washing active effect, spray, wet wipes or drops.

Concerning the components of the composition of the invention it is known from the literature that the Marigold (*Calendula officinalis*) contains flavonoids, saponines, phytosterols and ethereal oil. The tincture or tea prepared from Marigold is internally used for preventing stomach and intestinal ulcers, externally for the treatment of difficultly healing wounds as well as for vaginal irrigation and abolishment of vaginal flora (c.f. Mrs. Verzár: "Medical Plants in the Therapy"/in Hungarian/, Medicina, Budapest 1984, page 58; and H. A. Hoppe: "Drogenkunde", de Gruyter Verlag, Berlin 1981, page 480).

The crop of the Horse-chestnut (*Aesculus hyppocastanum*) contains aescin, quercetin, caempherol as well as flavonoids and cumarin derivatives. The extracts prepared from Horse-chestnut show anti-exudative properties and diminish the fragility of the blood vessels wall. Standardized compositions containing aescin are used for the treatment of lymphatic congestions, cerebral and lung oedemas as well as crural ulcer and hemorrhoids (Mrs. Verzár in her work cited above, page 92; as well as Hope in this work cited above, page 10).

Based on their characteristic sweetish taste, the extracts of Licorice (*Glycyrrhiza glabra*) are used as sweetening agent, seasoning agent and eventually as an expectorant (c.f. Issekutz in: "Prescription of Medicaments"/in Hungarian/, Medicina, Budapest 1972, page 578). By the systematic use of the standardized preparations, the increased tone of the stomach wall and the inflammatory state of the gastric mucosa can be diminished (c.f. Mrs. Verzár in her work cited above, pages 92 and 93).

The brew of Silver-weed is chiefly used internally as a spasmolytic agent (c.f. e.g. H-D. Braun: "Heilpflanzen-Lexikon für Ärzte und Apotheker", G. Fischer Verlag, Stuttgart 1974, page 155).

The aqueous extract of Walnut-tree leaves is used as an antiinflammatory agent. The teas prepared in the usual way (in the form of decoctions or brews) are used for treating skin diseases and skin inflammations (M. Pahlow: "Das grosse Buch der Heilpflanzen", Gräfe und Unzer GmbH, München 1979, page 344). Rarely, it is employed as a packing agent against ophthalmitis as well as for face-care.

The use of the ethereal oil of Lavender (*Lavendula officinalis seu vera*) is known. It is preferably used in refreshing, stimulating and antirheumatic baths. Its aqueous brew is used for packing in the popular medicine (for its use, c.f. M. Pahlow in his work cited above, page 213).

The Roman camomile (*Anthemis norbilis*) is a popular medicinal plant in several countries, e.g. France, where it has been introduced to the Pharmacopea, too. Except for the common component camazulene, its composition is strongly different from that of the camomile oil. Angelic acid and capric acid matricaria esters are its main constituents. It is widely used as a carminative and digestion-promoting agent. It is a particularly popular spasmolytic for treating the spastic conditions of the gastrointestinal tract (c.f. e.g. Mrs. Verzáar in her work cited above, page 55).

Further on, it should also be noted that the main active ingredients of the above 7 medicinal plants, i.e. flavonoids, tannic acids, aescin, glycyrrhizin and glycyrrhetic acid prepared in a native or artificial way, are used also by themselves in the form of concentrates or as the pure substance as active ingredients for cosmetics, para-medicaments and medicaments. Concerning the tanning agents, see the above-cited work of B. Issekutz (page 605). Many data on the other products are found in the "Rote Liste 1977/78", Bundesverband der Pharm. Industrie, Frankfurt 1978; as well as in A. Y. Leung: "Encyclopedia of Common Natural Ingredients", Wiley-Interscience Publ., New York 1980.

Thus, according to the literature, the individual components of the composition according to the invention are being used in the medicinal, cosmetic and popular medicinal practice though with a varying frequency; however, no composition corresponding or similar to the active ingredient composition according to the invention can be found in the descriptions published up to now.

Concerning the compositions of the instant invention, the preparation described in the Hungarian patent specification No. 190,391 cited above stands most close wherein 4 components are identical with the components of the composition according to the present invention although the concentration interval and the ratio of the components are different. In the patent specification cited above, 6 other components, i.e. willow-wood bark extract, oak-tree extract, garden sage extract, hop-concentrate, camomile oil and camomile extract, are described. The active ingredient content of the present invention is supplemented by 3 novel components in comparison to that described earlier: these are the extracts of the Marigold, Horse-chestnut and Licorice.

The activity of the composition according to the invention has been increased by the changes in the content in an unexpected way and extent in several directions. The outstanding effect of this novel composition consists in a multiplied antiinflammatory and calming effect.

Two representative compositions, i.e. a composition containing 5 components and one containing 10 components, respectively, of the Hungarian patent specification No. 190,391 were examined in comparison to the active ingredient composition of 7 components according to the present invention. The results can briefly be summarized as follows.

In the case of inhibition of the carrageenan (viscarin) oedema, the antiinflammatory effect of the novel composition was 5 to 20 times as high (i.e. by an order of magnitude higher) as that of the control products. These results are shown in FIG. 1. The antiinflammatory effect of the active ingredient consisting of 7 components according to the present invention is illustrated in curve A; that of the active ingredient consisting of 5 components according to the Hungarian patent specification No. 190,391 in curve B; and that of the composition consisting of 10 components according to the same Hungarian specification in curve C.

Figure 2:
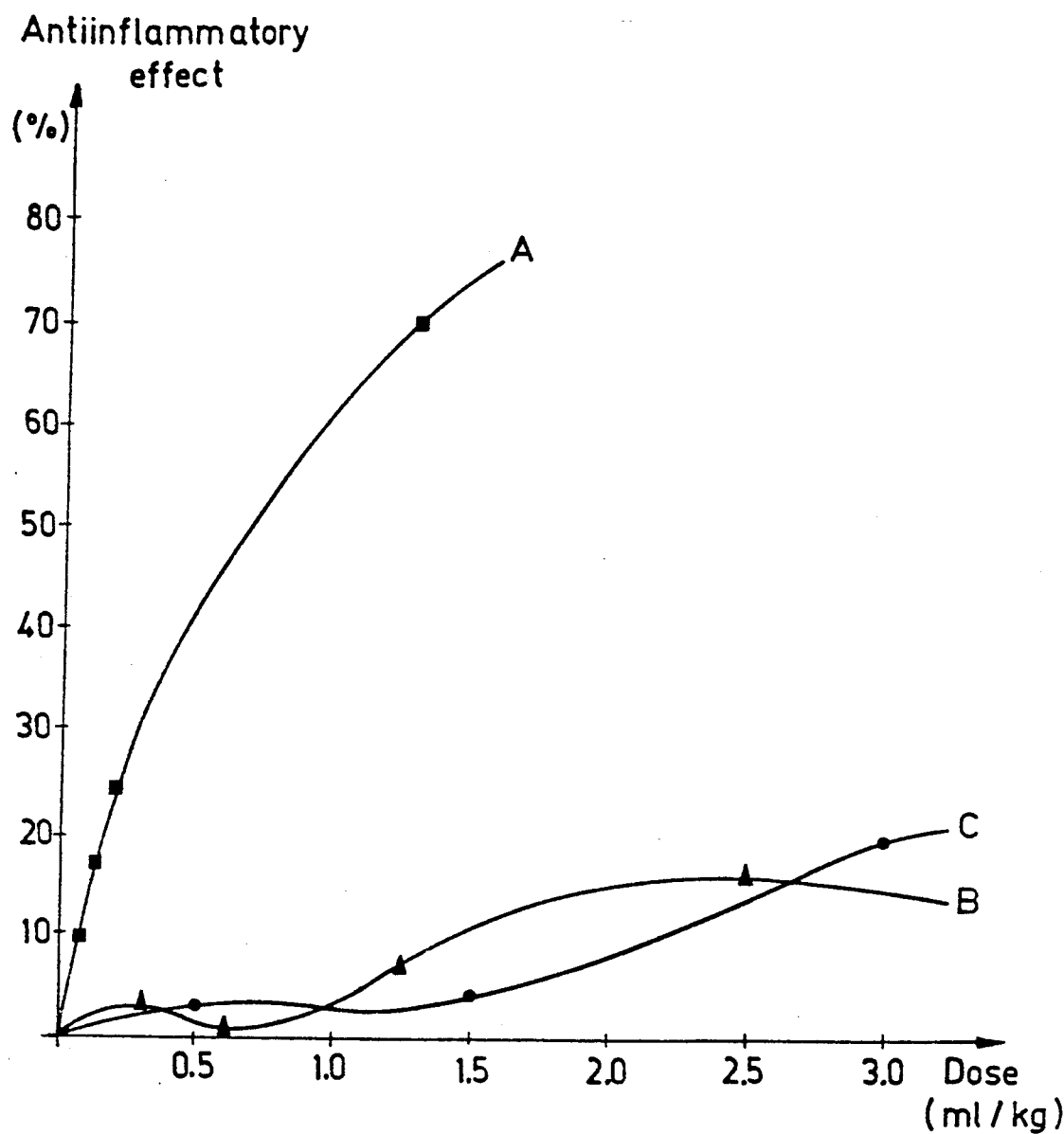

The advantage of the novel composition was even higher in the so-called serotonin oedema inhibition, wherein the effect increased to its 10 to 60-fold; more correctly, the effect of the control preparations was significant by using only high concentrations which were invaluable from a real viewpoint. The results are illustrated in FIG. 2 (for the symbols, see above).

The antiinflammatory action was studied on female CFY rats in such a way that an oedema-inducing agent (carrageenan or serotonin, respectively) was injected under the paw skin to elicit an oedema and then the volume of the paw was measured by a pletysmograph. The antiinflammatory agent was intraperitoneally administered to the animals by 30 minutes before the administration of the inflammation-inducing agent. The oedema developed was evaluated in the 5th or 1st hour, respectively, following the administration of the above two substances.

Figure 3:
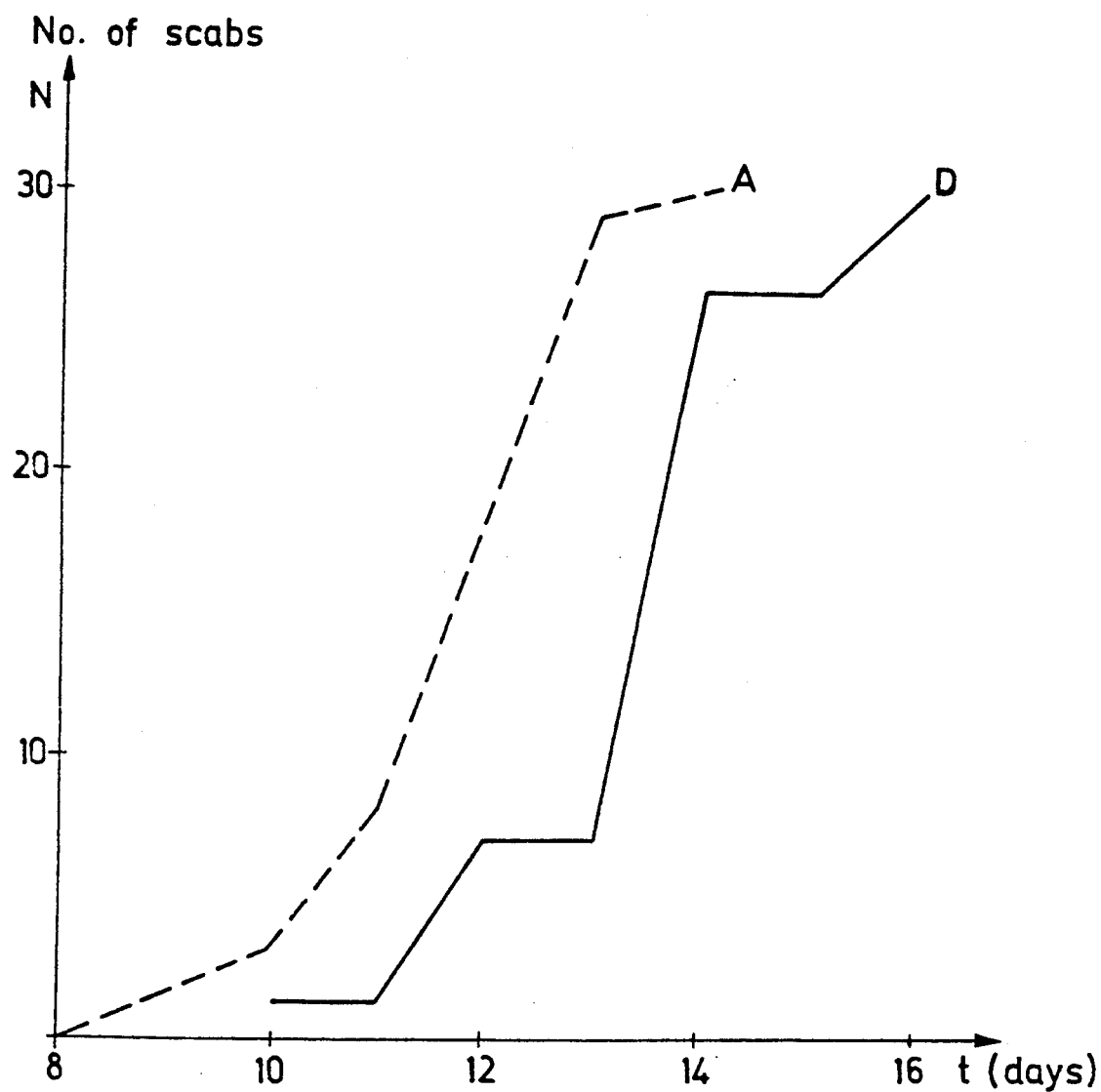

In addition to the outstanding antiinflammatory effect, the granulation-promoting action of the composition (signed by A in FIG. 3) can also be considered since it, based on the total number of the loosened scabs, abbreviated the healing of burns (elicited by focused light) by 2 days in comparison to physiological saline (signed by D in FIG. 3).

The examinations were similarly carried out on CFY rats. The burn was induced by a Tungsram 8 V 50 W projector glow-lamp used in the tail-flick equipment. The light source was placed in a distance of 4 cm and the treatment lasted 4 seconds. After depilating, 3 wounds each were inflicted on the unhaired skin of the animals 24 hours following the depilation. The treatment was continued daily twice until loosening of the last scab.

The above-described two main effects unambiguously indicate the possibility of using the novel composition both in the paramedicine and within the scope of the cosmetic compositions containing a biologically active ingredient.

In the paramedicine, the novel composition can be used for the treatment of hemorrhoids and other rectal complaints, burns, chiefly for curing inflammations following the burns by sun; for treatment of inflammations induced by chapping, abrasion simultaneously accompanied by epithelial lesions. Within these, the indications in the areas of sports and veterinary medicine are emphasized, with particular regard to competitors and competitory animals.

In the area of cosmetics, the composition according to the invention can preferably be used as an industrial protective composition; as a product serving the mass sports; and in some relations of treatment of dry and sensitive skin such as in calming baths, shower shampoos, hair-tonics for sensitive and scaly skin and the like. In both methods of use, the preparations containing the original composition serve also for the prevention, in addition to the treatment.

In the following, the individual properties and preparation of the components used in the combination of active ingredients, the preparation of the medicinal plant complex as well as the composition of the active ingredient preparations are summarized (the symbols a, b, c, d, e and f will be used in the Examples).

Characterization of the components 1) 40% alcoholic extract of Marigold (*Calendula officinalis flos*)

It is a yellowish-brown alcoholic liquid with an odour reminiscent of cognac, with a dry substance content of 3.5 to 4.5%. The pH value of the undiluted product is 5.0 to 6.5.

2) 60% alcoholic extract of Horse-chestnut (*Aesculus hippocastanum, semen*)

It is a yellowish-brown odourless or alcohol-smelling liquid with a direct pH value of 5.5 to 7.0 dry substance content of 6.5 to 7.5% and an aescin content of 0.65 to 0.75% (but of 10% calculated for the dry substance content).

3) 50% alcoholic extract of Licorice (*Glycyrrhiza glabra, radix*)

It is a yellowish-brown alcoholic liquid with a characteristic sweet odour. The pH value of the undiluted product is between 5.5 and 6.0. Its dry substance content amounts to 3.5 to 4.5%.

4) Aqueous Silver-weed (*Potentilla anserina herba*) extract concentrate

It is a brownish-black preparation with a characteristic odour reminiscent of the cooked sorrel and a thick, jam-like state. After diluting to 1:1 with water, its pH value is between 4 and 5. Its dry substance content amounts to 45 to 55% in the fresh state.

5) Aqueous Walnut-tree leaves (*Juglans regia, folium*) concentrate

It is a tar-like black mass with a mildly sweetish odour, with a dry substance content of 45 to 55% in the fresh state. After dilution to 1:1 with water, its pH value is between 4 and 6.

6) Lavender resinoid (*Lavendula officinalis, herba*)

It is a dark-green, jam-like mass with a characteristic odour of Lavender. After shaking 1 part of it with 50 parts of water, the solution shows a pH value of 3 to 4.5.

7) Roman camomile oil (*Anthemis nobilis, flos*)

It is a dark-green, mobile oil in a fresh state with a characteristic odour, which becomes yellowish-brown while standing, particularly under effect of light, with a viscosity of $8 \pm 4$ mPa.s. After shaking 1 part of it with 50 parts of water, the solution shows a pH value of 3 to 4.5.

Preparation of the compounds

1) Aqueous-ethanolic extract of Marigold

The flowers are defatted by solvents (chloroform, methylene chloride) and removing the solvents the flowers are extracted by mixing with 40% aqueous ethanol under vigorous stirring for 2 hours. Thereupon the extract is flown off, the drug is thoroughly pressed out and the combined extract is adjusted to an 1.6:10 ratio of the drug to the extract. The extract is left to stand at $-15°$ C. for 24 hours and then filtered to clear.

2) Aqueous-ethanolic extract of the Horse-chestnut

It is extracted by using 60% ethanol from the broken crop of *Aesculus hippocastanum* L. The prescription involves a dry substance content of 6.5 to 7.5% for the final product and the dry substance should contain over 10% of aescin. The ethanol content amounts to 56 to 60%.

3) Aqueous-ethanolic extract of Licorice

It is prepared by extracting the dried and pulverized root of *Glycyrrhiza glabra* with 50% ethanol. The drug is extracted by an about 10fold amount of 50% ethanol while vigorous stirring for 2 hours. Then, the extract is filtered off, the filtrate is diluted to a 4:10 ratio of the drug to the extract by using 50% ethanol and then filtered to clear. The extract is always prepared in a fresh state and used for preparing the complex within 2 to 3 days.

4) Aqueous extract of Silver-weed

The dried over-earth part (stem, leaves and flower) of Potentilla anserina L. are soaked in a 10 fold amount of water suitably at a temperature of 55° C. This temperature is maintained for 4 hours, then the extract obtained is filtered off and evaporated suitably under a pressure of 6 kPa.

5) Aqueous extract of Walnut-tree leaves

The dried leaves of Juglans regia L. are soaked in a 10 fold amount of water suitably at a temperature of 55° C. After maintaining this temperature for 4 hours and then filtering off, the aqueous extract is suitably evaporated under a pressure of 6 kPa.

6) Lavender resinoid

It is obtained by extracting the 1 year old flower and stem of Lavendula officinalis L. after evaporation of the ethereal oils and drying. The dried and chopped plant is first subjected to an extraction by methylene chloride and after evaporation of the solvent, the Lavender resinoid is obtained as the residue of the extract.

7) Roman camomile oil

This is the ethereal oil obtained by steam distillation of the flower and stem of Anthemis nobilis L. The given species does not grow in a wild form in Hungary but its improved variety is cultivated. The oil should not contain any plant protective agent in an amount detectable by gas-liquid chromatography. The plant material is treated in stainless steel vessel equipped with a distilling pipe and cooling coil by steam under a pressure of 300 to 400 kPa at optimum distillation rate of 80 to 100 litres/hour. The ethereal oil is taken up in Florentini glass bottles.

Preparation of the medicinal plant complex

After dissolving the Lavender resinoid and Roman camomile oil in the weighed amount of 96% ethanol, the Marigold extract, optionally the Licorice extract as well as the Horse-chestnut extract are added to the solution under stirring. The extract concentrates of the Walnut-tree leaves and Silver-weed are dissolved in distilled water or aqueous ethanol and the additive thus-obtained is mixed with the solution containing the other components. Subsequently, the alcohol content of the system is suitably adjusted to 50% by weight and then filtered. After a storage of 2 to 3 days, the preparation is filtered to completely clear.

| The labeling of the active ingredient combinations (a to f) in the Examples | | | | | | |
|---|---|---|---|---|---|---|
| | % by weight | | | | | |
| | a | b | c | d | e | f |
| Marigold extract | 0.05 | 0.5 | 0.5 | 1.0 | 2.0 | 3.0 |
| Horse-chestnut extract | 0.05 | 0.5 | 1.0 | 1.0 | 1.5 | 1.5 |
| Licorice extract | 0.05 | 0.25 | 0.5 | 1.0 | 0.5 | 1.0 |
| Silver-weed extract | 0.05 | 0.5 | 0.5 | 1.0 | 1.0 | 1.5 |
| Walnut-tree leaves extract | 0.05 | 0.25 | 0.5 | 0.5 | 1.0 | 1.0 |
| Lavender resinoid | 0.02 | 0.25 | 0.5 | 0.25 | 0.5 | 0.5 |
| Roman camomile oil | 0.005 | 0.05 | 0.1 | 0.05 | 0.1 | 0.15 |
| furthermore as vehicles: | | | | | | |
| 35.0% by weight ethanol | 99.725 | 97.7 | — | — | — | — |
| 50.0% by weight ethanol | — | — | 96.4 | 95.2 | — | — |
| 60.0% by weight ethanol | — | — | — | — | 93.4 | 91.35 |

The invention is illustrated in detail by the following non-limiting Examples. In these Examples, the total amount of the active ingredients is given for the total weight of the active ingredients and aqueous ethanol. Based on this definition, the total active ingredient content can amount to 2 to 50% by weight as calculated for the total weight of the composition.

EXAMPLES 1 TO 4

Preparation of creams

The creams are prepared from three phases, i.e. from the so-called phases A, B and C. The components of the separate phases are defined in tables.

In a double-wall mixing vessel, the phase B is preheated to a temperature between 67° and 82° C., the phase A is added at an approximately similar temperature under stirring, then the mixture is stirred mostly at a high speed of rotation without cooling. Thereupon, the stirring is continued at a lower rotation speed while beginning the gradual cooling of the mixture. When the temperature of the system reaches about 50° C., the phase C is added under stirring and the stirring is continued until the mixture is cooled down.

These 4 creams are suggested to be used as a veterinary antiinflammatory composition, a paramedicine against hemmorrhoid, sport cream and industrial protective cream, respectively.

| Components, % by weight | No. of Example | | | |
|---|---|---|---|---|
|  | 1 | 2 | 3 | 4 |
| Phase A |  |  |  |  |
| Liquid paraffin | 18 | 5 | — | 8 |
| Stearin | 7 | — | 6 | — |
| Polyoxyethylene fatty acid ester | 6 | — | 6 | — |
| Isooctyl stearate | 4 | — | 8 | — |
| Glycerol monostearate | — | 10 | — | — |
| $C_{8-12}$ fatty acid triglycerides | — | 8 | 6 | — |
| Decyl oleate | — | 5 | — | — |
| Cetyl alcohol | — | 2 | 2 | 4 |
| Stearyl alcohol | — | 2 | — | 2 |
| 2-Octyldodecanol | — | 2 | — | — |
| Paraffin wax | — | — | 2 | — |
| Polyoxyethylene-sorbitan monolaurate containing 20 moles of ethylene oxide | — | — | — | 4.5 |
| Silicone oil (1000 mPa · s) | — | — | — | 3 |
| Phase B |  |  |  |  |
| Distilled water | 39 | 49.6 | 55.2 | 56.4 |
| Propylene glycol | 3.8 | 5 | 3.8 | 4.5 |
| Glycerol 86% | 5 | — | 5 | 14 |
| Allantoin | — | — | 0.2 | — |
| 2,4,4'-Trichloro-2-hydroxydiphenyl ether | — | — | — | 0.1 |
| Sorbic acid | 0.1 | 0.1 | 0.1 | 0.1 |
| Potassium sorbate | 0.1 | 0.1 | 0.1 | 0.1 |
| Phase C |  |  |  |  |
| Medical plant combination | $15^d$ | $10^e$ | $5^c$ | $2^b$ |
| Glycerol-polyethylene glycol oxystearate containing 45 moles of ethylene oxide | 2 | — | — | 1 |
| Polyoxyethylene glycerol monolaurate containing 30 moles of ethylene oxide | — | 1 | 0.5 | — |
| Fragrance | — | — | 0.1 | 0.1 |

EXAMPLES 5 TO 7

Preparation of liquid emulsions

The liquid emulsions are prepared from two main phases (A and B) and two or three additive phases (C and E and C, D and E, respectively). The composition of the phases are indicated below.

The materials of the fatty phase A are melted together under stirring at a temperature of about 70° C. Simultaneously, the aqueous phase B is prepared in such a way that the "cold" distilled water is mixed with the propylene glycol or glycerol and the carboxyvinyl copolymer (additive phase C) is swollen or dissolved, respectively, therein. After adjusting the temperature to about 72° C., the aqueous phase is mixed with the fatty phase while stirring. After carrying out an intense chopping for 5 to 10 minutes, an aqueous solution of sodium hydroxide (phase D) is optionally (Example 6) added to the system. Then, the emulsion is started to cool under constant stirring and the additive phase E, i.e. the medicinal plant composition is added to the emulsion at a temperature of about 50° C. Finally, the stirring is continued until the mixture cools down.

The 3 liquid emulsions are suggested to be used as a sport milk, as a body hygienic composition for men and as a calming emulsion against burns, respectively.

| Components, % by weight | No. of Examples | | |
|---|---|---|---|
|  | 5 | 6 | 7 |
| Phase A |  |  |  |
| Triglycerides of $C_{8-12}$ fatty acids | 8 | — | 14 |
| Isooctyl stearate | 5 | 7 | — |
| Polyoxyethylene(5)-stearyl stearate | 4 | — | — |
| Polyoxyethylene-cetostearyl alcohol ether | 2 | — | — |
| Liquid paraffin | — | 7 | 2 |
| Wool fat | — | 3 | — |
| Polyoxyethylene-sorbitan monostearate containing 20 moles of ethylene oxide | — | 3 | — |
| Lauryl tetraglycol ether O-phosphoric acid ester | — | — | 3 |
| Phase B |  |  |  |
| Distilled water | 71.9 | 69.11 | 69.70 |
| Propylene glycol | 3.8 | — | 3 |
| Glycerol | — | 3 | — |
| Additive phase C |  |  |  |
| Carboxyvinyl copolymer | — | 0.15 | 0.5 |
| Additive phase D |  |  |  |
| Sodium hydroxide | — | 0.04 | 0.2 |
| Additive phase E |  |  |  |
| Medicinal plant combination | $5^c$ | $3^a$ | $8^d$ |
| Menthol | 0.1 | — | — |
| Natural moisturizing factor | — | 2 | — |
| d-Panthenol | — | — | 0.5 |
| Fragrance | 0.2 | 0.2 | 0.1 |

EXAMPLES 8 TO 10

Foam bath, shower bath and shampoo compositions

The washactive concentrates are usually prepared from 4 phases. Phase A is prepared by mixing the components in the above succession; then phase B is added and thoroughly mixed therein. After adding the following phase C, i.e. the active ingredient combination, the mixture is stirred for 5 minutes. Phase 4 is the aqueous solution of sodium lauryl ether sulfate which is similarly mixed under stirring to the system.

These 3 compositions can be used for the preparation of a calming foam bath, sport and home douche shampoo, respectively.

| Components, % by weight | No. of Examples | | |
|---|---|---|---|
|  | 8 | 9 | 10 |
| Phase A |  |  |  |
| Coconut fatty acid amide propyl- | 15 | 20 | — |

| Components, % by weight | No. of Examples | | |
|---|---|---|---|
| | 8 | 9 | 10 |
| betaine (50%) | | | 30 |
| Propylene glycol ether sulfosuccinate (40%) | — | — | |
| Distilled water | 42.2 | 23.7 | 30.2 |
| Alkyl ether sulfate and a composition ensuring pearly lustre | — | 3 | 5 |
| Coconut fatty acid diethanolamide | — | 1 | 2 |
| Sodium chloride | 2 | 1 | — |
| Citric acid | — | 0.3 | 0.3 |
| Phase B | | | |
| Polyethylene glycol glyceryl monococoate | 2 | 3 | 3 |
| Ethoxylated alkylphenol and 2-ethylhexenoic acid polyethylene glycol ester | 1 | 1.5 | 1 |
| Flavour composition | 0.8 | 0.5 | 0.5 |
| Phase C | | | |
| Medical plant combination | 5$^c$ | 10$^d$ | 3$^f$ |
| Phase D | | | |
| Sodium lauryl ether sulfate (30%) | 30 | 40 | 25 |

EXAMPLES 11 TO 17

Solution compositions which can be formulated as cloth, spray and painting preparations These products can be prepared by mixing the components. The succession of mixing can be carried out according to the list given below. The solutions prepared are filtered in a suitable filtering device, e.g. on a Seitz filter directly after preparation, more preferably after standing for 24 hours.

The main indications of the solutions defined in the Examples are as follows:

11) industrial protective and calming spray;
12) and 13) calming and refreshing sport-spray;
14) anti-hemorrhoid spray;
15) a base solution for anti-hemorrhoid wet wipes;
16) and 17) antiinflammatory and refreshing preparations for the veterinary medicine.

| Components, % by weight | No. of the Examples | | | | | | |
|---|---|---|---|---|---|---|---|
| | 11 | 12 | 13 | 14 | 15 | 16 | 17 |
| Medical plant combination | 10$^b$ | 10$^e$ | 20$^c$ | 20$^b$ | 40$^d$ | 15$^b$ | 30$^d$ |
| Ethanol 96% by weight | 16 | 10 | 12 | — | — | — | — |
| Glycerol | 10 | 12 | 15 | — | — | — | — |
| Propylene glycol | — | 5 | — | — | — | — | 7 |
| Distilled water | 63.5 | 62.5 | 52.5 | 76.8 | 58 | 81.8 | 60 |
| Polyoxyethylene-sorbitan monooleate containing 20 moles of ethylene oxide | 0.5 | 0.5 | 0.5 | 3 | — | 3 | 3 |
| Polydocanol | — | — | — | — | 2 | — | — |
| Potassium sorbate | — | — | — | 0.1 | — | 0.1 | — |
| Sorbic acid | — | — | — | 0.1 | — | 0.1 | — |

We claim:

1. A composition with an antiinflammatory and skin antiirritant effect, which comprises, based on the total weight of the composition, 0.005 to 5.0% by weight of an aqueous-ethanolic extract of Marigold 0.005 to 2.0% by weight of an aqueous-ethanolic extract of Horse-chestnut, 0.005 to 2.0% by weight of an aqueous-ethanolic extract of Licorice (sweet-root), 0.005 to 2.0% by weight of an aqueous Silver-weed extract, 0.005 to 2.0% by weight of an aqueous extract of Walnut-tree leaves, 0.005 to 2.0% by weight of an Roman camomile oil, and 85% to 99% by weight of an ethanol-water mixture as carrier.

2. A cosmetic or paramedicinal product, which comprises
   1 to 50% by weight of the composition as claimed in claim 1 and 50 to 99% by weight of a further component selected from the group consisting of: water, glycerol, propylene glycol, polyethylene glycol, polyoxyethylene-sorbitan fatty acid ester, wax alcohols, coconut fatty acid diethanol-amide, coconut fatty acidpropyl-betaine, a solubilizing agent, a stabilizing agent, a flavor composition and mixtures thereof.

3. The cosmetic or paramedicinal product of claim 2 which further comprises a component selected from the group consisting of:
   0.01 to 5% by weight of menthol
   0.02 to 5% by weight of citric acid,
   0.02 to 1.0% by weight of d-panthenol,
   0.05 to 0.5% by weight of allantoin,
   0.05 to 2.0% by weight of 2,4,4'-trichloro-2-hydroxydiphenyl ether, and
   0.5% to 50.0% by weight of ethanol, and mixtures thereof.

* * * * *